(12) United States Patent
Dargazanli et al.

(10) Patent No.: US 7,790,753 B2
(45) Date of Patent: *Sep. 7, 2010

(54) DERIVATIVES OF N-[PHENYL(ALKYLPIPERIDINE-2-YL)METHYL]BENZAMIDE, PREPARATION METHOD THEREOF AND APPLICATION OF SAME IN THERAPEUTICS

(75) Inventors: Gihad Dargazanli, Cachan (FR); Genevieve Estenne-Bouhtou, Chevilly-Larue (FR); Corinne Veronique, Antony (FR)

(73) Assignee: sanofi-aventis, Paris (FR)

( * ) Notice: Subject to any disclaimer, the term of this patent is extended or adjusted under 35 U.S.C. 154(b) by 1092 days.

This patent is subject to a terminal disclaimer.

(21) Appl. No.: 11/405,285

(22) Filed: Apr. 17, 2006

(65) Prior Publication Data
US 2006/0223861 A1 Oct. 5, 2006

Related U.S. Application Data

(63) Continuation of application No. PCT/FR2004/002642, filed on Oct. 15, 2004.

(30) Foreign Application Priority Data

Oct. 17, 2003 (FR) .................................. 03 12141

(51) Int. Cl.
A61K 31/445 (2006.01)
C07D 211/32 (2006.01)

(52) U.S. Cl. ................... 514/331; 514/241; 514/249; 514/256; 514/307; 514/311; 514/318; 514/321; 514/322; 514/324; 514/326; 546/113; 546/114; 546/115; 546/139; 546/152; 546/194; 546/198; 546/199; 546/200; 546/201; 546/205; 546/209; 546/211; 546/212; 546/214; 544/212; 544/288; 544/333; 544/349; 544/353

(58) Field of Classification Search ............. 514/241, 514/249, 256, 307, 311, 318, 321, 322, 324, 514/326, 331; 546/113, 114, 115, 139, 152, 546/194, 198, 199, 201, 205, 209, 210, 211, 546/212, 214, 234; 544/212, 288, 333, 349, 544/353
See application file for complete search history.

(56) References Cited

U.S. PATENT DOCUMENTS

| 3,801,636 | A | 4/1974 | Horrom | |
|---|---|---|---|---|
| 5,254,569 | A | 10/1993 | Cheeseman et al. | |
| 5,364,868 | A | 11/1994 | Englert et al. | |
| 7,205,319 | B2 * | 4/2007 | Dargazanli et al. | 514/331 |
| 7,226,917 | B2 | 6/2007 | Dargazanli | |
| 7,288,656 | B2 | 10/2007 | Dargazanli | |
| 7,300,946 | B2 * | 11/2007 | Ding et al. | 514/317 |
| 7,326,722 | B2 * | 2/2008 | Dargazanli et al. | 514/331 |
| 7,326,732 | B2 * | 2/2008 | Oxford et al. | 514/613 |
| 7,335,670 | B2 * | 2/2008 | Dargazanli et al. | 514/318 |
| 2007/0155789 | A1 | 7/2007 | Dargazanli et al. | |
| 2007/0197601 | A1 | 8/2007 | Dargazanli | |
| 2007/0208006 | A1 | 9/2007 | Dargazanli | |
| 2008/0070941 | A1 | 3/2008 | Dargazanli | |

FOREIGN PATENT DOCUMENTS

| EP | 0499995 | 8/1992 |
|---|---|---|
| EP | 0556672 | 8/1993 |
| WO | WO 99/45011 | 9/1999 |
| WO | WO2006/110724 | * 10/2006 |

OTHER PUBLICATIONS

Harsing et al. "Glycine transporter type-1 and its inhibitos" Current Medi. Chem. v.13, p. 1017-1044 (2006).*
Wermuth "The practice of medicinal chemistry" p. 203-207 (1996).*
Dutta et al. "Potent and selective ligand . . . " J. Med. chem. v.41 (5), p. 699-705 (1998).*

(Continued)

Primary Examiner—Celia Chang
(74) Attorney, Agent, or Firm—Kelly L. Bender

(57) ABSTRACT

Compounds of formula (I) as defined herein:

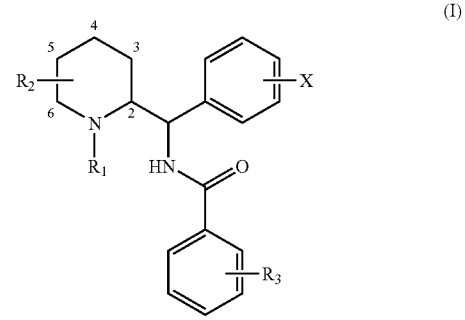

are useful for treating behavioral disorders associated with dementia, psychoses, in particular schizophrenia (deficient form and productive form) and acute or chronic extrapyramidal symptoms induced by neuroleptics; for the treatment of various forms of anxiety, panic attacks, phobias, and compulsive obsessive disorders; for treating various forms of depression, including psychotic depression; for treating disorders caused by alcohol abuse or weaning from alcohol, sexual behavior disorders, eating disorders and for treating migraine. Moreover, the compounds of the invention may be used for treating painful muscle contracture in rheumatology and in acute spinal pathology; for treating spastic contractures of medullary or cerebral origin; for the symptomatic treatment of acute and subacute pain of light to moderate intensity; for treating intense and/or chronic pain, neurogenic pain and intractable pain; for treating Parkinson's disease and Parkinson-like symptoms of neurodegenerative origin or induced by neuroleptics; for treating partial primary and secondary generalized epilepsy of simple or complex symptomology, mixed forms and other epileptic syndromes in addition to another antiepileptic treatment, or in monotherapy, for the treatment of sleep apnea, and for neuroprotection.

8 Claims, No Drawings

OTHER PUBLICATIONS

Braga et al."Making crystals . . . " Chem. Commun. p. 3635-3645 (2005).*

Leonetti et al. "2-chloro-N-phenyl . . . " Neuroscience v.137, p. 555-564 (2006).*

Sur et al. "Glycine transporter 1 . . . " Current Drug Target, v. 8, p. 643-649 (2007).*

Beak et al, Alpha-Lithioamine Synthetic Equivalents: Syntheses of Diastereoisomers from Boc Derivatives of Cyclic Amines, J. Org. Chem. 1993, 58, pp. 1109-1117.

Beak et al, Alpha-Lithioamine Synthetic Equivalents: Syntheses of Diastereoisomers from the Boc Piperidines, J. Org. Chem. 1990, 55, pp. 2578-2580.

Froelich, O., et, al., Asymmetric Synthesis, 39. 1 Synthesis of 2-(1-Aminoalkyl)Piperidines via 2-Cyano-6-Phenyl Oxazolopiperidine, J. Org. Chem. (1996) vol. 61, pp. 6700-6705.

Hodgson et al, III. 3-Nitro-4-amino- and the 3:4-Dihalogenobenzaldehydes, J. Chem. Soc. 1927, pp. 20-27.

Jeong et al, A New Method for the Preparation of Perfluoroalkylated Triphenylethylene Derivatives, Tetrahedron Letters, 1996 (37) 33, pp. 5905-5908.

Jonathan H. Lebowitz, A breach in the blood-brain barrier, PNAS (2005, pp. 14485-14486, vol. 102, No. 41).

Martinelli et al, Aromatic Chlorination of p-Aminobenzoic Acid Derivatives, Improved Syntheses of Mono- and Dichloromethotrexate, J. Org. Chem. 1980 (45) pp. 527-529.

Mel R., Optical Isomers , Optical Isomers Newton BBS, (2006), Newton.dep.ant.gov.

Ohmomo et al, Synthesis and Evaluation of Iodinated Benzamide Derivatives as Selective and Reversible Monoamine Oxidase B Inhibitors, Chem. Pharm. Bull. 1992 (40) 7, pp. 1789-1792.

Richard Daneman et al., The Blood-Brain Barrier—Lessons from Moody Flies, Cell (2005, pp. 9-12, vol. 123, No. 1).

Sato et al, A new entry to 9-azabicyclo[3.3.1]nonanes using radical translocation/cyclisation reactions of 2-(but-3-ynyl)-1-(o-iodobenzoyl)piperidines, J. Chem. Soc., Perkin Trans 1, 2002, pp. 1438-1443.

Wilson L. Caulfield et al., The First Potent and Selective Inhibitors of the Glycine Transporter Type 2, Journal of Medicinal Chemistry (2001, pp. 2679-2682, vol. 44, No. 17).

Woods, et. al., Method of Treating Schizophrenia Prodome, CA 145:432223 (2006).

U.S. Appl. No. 12/407,276, filed Mar. 19, 2009, Dargazanli.

Stewart et al, Synthesis of Substituted 9-Oxo-9,10-dihydroacridine-4-carboxylic Acids. I. Factors Affecting the Direction of Ring Closure of Substituted N-(2-Carboxyphenylamino)benzoic Acids, Aust. J. Chem., 1984 (37) pp. 1939-1950.

* cited by examiner

DERIVATIVES OF N-[PHENYL(ALKYLPIPERIDINE-2-YL) METHYL]BENZAMIDE, PREPARATION METHOD THEREOF AND APPLICATION OF SAME IN THERAPEUTICS

CROSS-REFERENCE TO RELATED APPLICATIONS

This application is a continuation of PCT/FR2004/002642, filed Oct. 15, 2004, which claims priority from French Patent Application No. 0312141, filed Oct. 17, 2003.

SUMMARY OF THE INVENTION

The compounds of the invention correspond to the general formula (I)

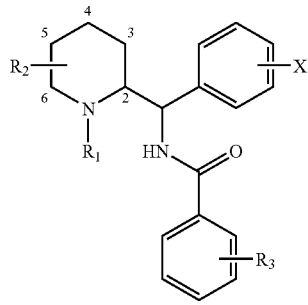

in which $R_1$ represents either a hydrogen atom, or a linear or branched ($C_1$-$C_7$)alkyl group optionally substituted with one or more fluorine atoms, or a ($C_3$-$C_7$)cycloalkyl group, or a ($C_3$-$C_7$)cycloalkyl($C_1$-$C_3$)alkyl group, or a phenyl($C_1$-$C_3$) alkyl group optionally substituted with one or two methoxy groups, or a ($C_2$-$C_4$)alkenyl group, or a ($C_2$-$C_4$)alkynyl group;

$R_2$ represents either a linear or branched ($C_1$-$C_7$)alkyl or ($C_3$-$C_7$)cycloalkyl group, or a ($C_3$-$C_7$)cycloalkyl($C_1$-$C_3$) alkyl group;

X represents either a hydrogen atom or one or more substituents chosen from halogen atoms and trifluoromethyl, linear or branched ($C_1$-$C_6$)alkyl and ($C_1$-$C_6$)alkoxy groups;

$R_3$ represents either a hydrogen atom or one or more substituents chosen from halogen atoms and trifluoromethyl, linear or branched ($C_1$-$C_6$)alkyl, ($C_3$-$C_7$)cycloalkyl, ($C_1$-$C_6$) alkoxy, phenyl, cyano, acetyl, benzoyl, ($C_1$-$C_6$)thioalkyl, ($C_1$-$C_6$)alkylsulfonyl, carboxyl and ($C_1$-$C_6$)alkoxycarbonyl groups, or a group of general formula $NR_4R_5$ or $SO_2NR_4R_5$ or $CONR_4R_5$ in which $R_4$ and $R_5$ each independently represent a hydrogen atom or a linear or branched ($C_1$-$C_6$)alkyl or ($C_3$-$C_7$)cycloalkyl group, or $R_4$ and $R_5$ form, with the nitrogen atom that bears them, a pyrrolidine, piperidine or morpholine ring.

BACKGROUND OF THE INVENTION

Compounds of structure similar to that of the compounds of the invention are described in U.S. Pat. No. 5,254,569 as analgesics, diuretics, anticonvulsivants, anesthetics, sedatives and cerebroprotective agents, via a mechanism of action on the opiate receptors. Other compounds of similar structure are described in patent application EP-0 499 995 as 5-$HT_3$ antagonists that are useful in the treatment of psychotic disorders, neurological diseases, gastric symptoms, nausea and vomiting.

DETAILED DESCRIPTION OF THE INVENTION

The compounds of formula (I) contain two or three asymmetric centers depending on whether $R_2$ is in position 2, 3, 4, 5 or 6. They may thus exist in the form of enantiomers or diastereoisomers. These enantiomers and diastereoisomers, and also mixtures thereof, including racemic mixtures, form part of the invention.

More particularly, the compounds of formula (I) may exist in the form of threo ((1S,2S) and (1R,2R)) or erythro ((1S,2R) and (1R,2S)) enantiomers or diastereoisomers with a cis or trans stereochemistry of the piperidine substituents, or as a mixture of such isomers.

The compounds of formula (I) may exist in the form of bases or of acid-addition salts. Such addition salts form part of the invention.

The salts are advantageously prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

The compounds of the invention show particular activity as specific inhibitors of the glycine transporters glyt1 and/or glyt2.

The compounds of general formula (I) in which $R_1$ is other than a hydrogen atom may be prepared via a process illustrated by Scheme 1 below.

Scheme 1

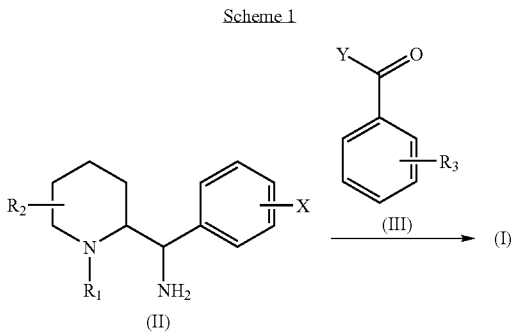

Coupling of a diamine of general formula (II), in which $R_1$, $R_2$ and X are as defined above (with $R_1$ other than a hydrogen atom), with an activated acid or an acid chloride of general formula (III) in which Y represents an activated OH group or a chlorine atom and $R_3$ is as defined above, is performed using the methods known to those skilled in the art.

The diamine of general formula (II) with $R_2$ in position 3, 4, 5 or 6 may be prepared via a process illustrated by Scheme 2 below.

According to a first route, the α-lithiation of the piperidine of general formula (IV), in which $R_2$ is as defined above and Boc represents a 1,1-dimethylethoxy-carbonyl group, is performed with sec-butyllithium in the presence of TMEDA (N,N,N',N'-tetramethylethylenediamine) in an ether solvent such as diethyl ether at −78° C., to react the lithioamine formed in situ with the benzaldehyde derivative of general formula (VI), in which X is as defined above. A mixture of alcohol of general formula (VIII) and of cyclic carbamate of general formula (IX) is thus obtained.

These compounds may also be obtained according to a second route in the following manner: the aldehyde of general formula (V) is either prepared according to methods described in the literature, or prepared from the piperidine of general formula (IV) after lithiation and condensation with the dimethylformaldehyde under the conditions described above. It is then reacted with the derivative of general formula (VII), in which X is as defined above and M represents a metal such as lithium, in an ether solvent such as diethyl ether, between −30° C. and room temperature, to give the compounds of general formulae (VIII) and (IX). The alcohol of general formula (VIII) of threo/erythro configuration is converted into the alcohol of general formula (XI) of threo configuration in two steps in the following manner: the alcohol is oxidized to the ketone of general formula (X) with an oxidizing agent such as pyridinium chlorochromate in a chlorinated solvent such as dichloromethane at room temperature, and the ketone is then diastereoselectively reduced to an alcohol of threo configuration of general formula (XI) with a reducing agent such as K-Selectride® or L-Selectride® (potassium or lithium tri-sec-butylborohydride), in an ether solvent such as tetrahydrofuran, between −78° C. and room temperature.

The carbamate of general formula (XI) of threo configuration may then be reduced to the threo N-methylamino alcohol of general formula (XII) via the action of a mixed hydride such as lithium aluminum hydride, in an ether solvent such as tetrahydrofuran, between room temperature and the reflux temperature. Under the same reduction conditions, the threo cyclic carbamate of general formula (IX) also leads to the threo N-methylamino alcohol derivative of general formula (XII).

The threo/erythro cyclic carbamate mixture of general formula (IX) leads to the mixture of threo/erythro derivatives of general formula (XII), which may be purified and separated by chromatography on silica gel to give the pure threo compound and the pure erythro compound.

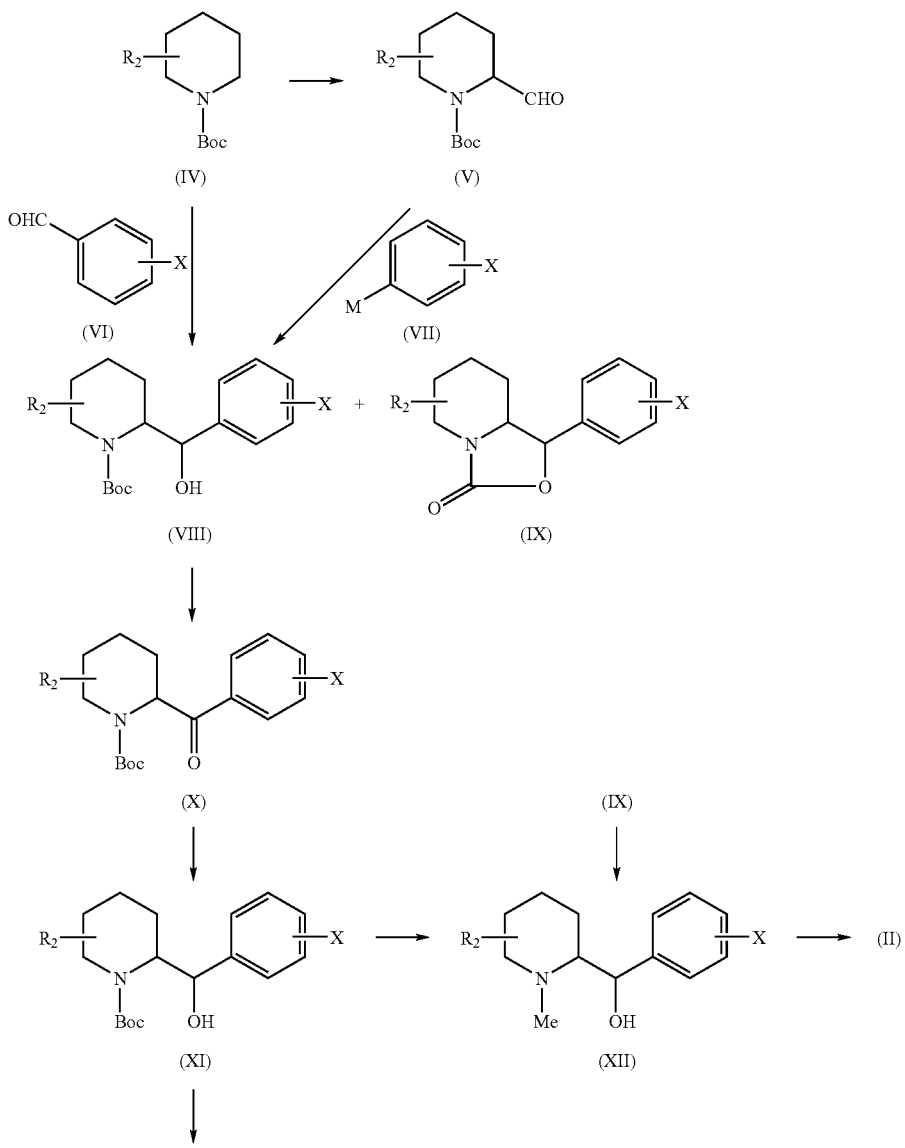

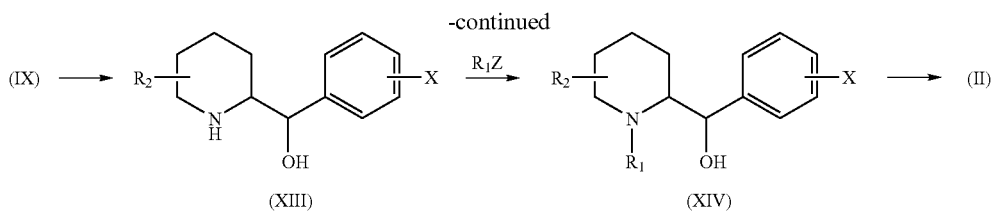

The threo alcohol of general formula (XII) is then converted into the threo intermediate of general formula (II) in which $R_1$ represents a methyl group, in two steps: the alcohol function is first converted into an electrophilic group, for example a methanesulfonate group, via the action of methanesulfonyl chloride, in a chlorinated solvent such as dichloromethane, and in the presence of a base such as triethylamine, between 0° C. and room temperature, and the electrophilic group is then reacted with liquefied ammonia at −50° C., in an alcohol such as ethanol, in a closed medium such as an autoclave, between −50° C. and room temperature.

The carbamate of general formula (XI) of threo configuration may also be deprotected using a strong base such as aqueous potassium hydroxide, in an alcohol such as methanol to obtain the threo amino alcohol of general formula (XIII). Under the same hydrolysis conditions, the cyclic carbamate of general formula (IX) leads to the amino alcohol of general formula (XIII).

An N-alkylation is then performed using a halogenated derivative of formula $R_1Z$, in which $R_1$ is as defined above, but other than a hydrogen atom, and Z represents a halogen atom, in the presence of a base such as potassium carbonate, in a polar solvent such as N,N-dimethylformamide, between room temperature and 100° C., to give the alkylated derivative of general formula (XIV). The alkylated derivative of general formula (XIV) is then transformed into the intermediate of general formula (II) as described with respect to the alcohol of general formula (XII).

The process may be performed in the same manner as above with the erythro derivatives of general formula (IX) to obtain the erythro compounds of general formula (I).

The diamine of general formula (II) with $R_2$ in position 2 may be prepared via a process illustrated by Scheme 3 below.

Scheme 3

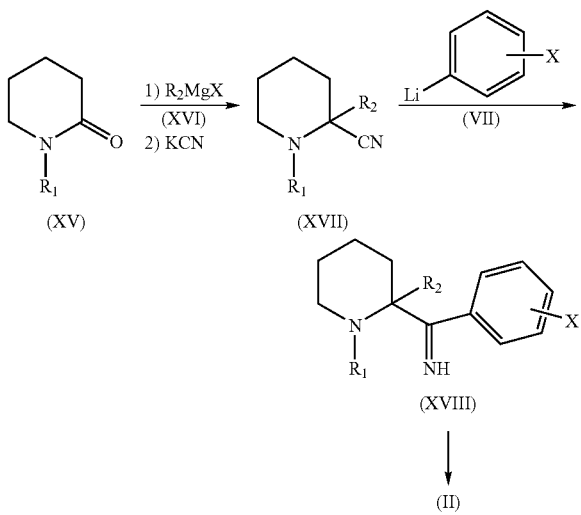

A piperidinone of general formula (XV), in which $R_1$ is as defined above, is reacted with an organometallic reagent of general formula (XVI), in refluxing tetrahydrofuran, and the reaction medium is treated with potassium cyanide solution to give the amino nitrile of general formula (XVII). This product is then reacted with a lithiated derivative of general formula (VII), in which X is as defined above, in an ether solvent such as diethyl ether or tetrahydrofuran, between −90° C. and −30° C.; an intermediate imine of general formula (XVIII) is obtained, which is reduced to the threo primary amine of general formula (II) with a reducing agent such as sodium borohydride, in a protic solvent such as methanol, between 0° C. and room temperature.

The compounds of general formula (I) in which $R_1$ represents a hydrogen atom may be prepared from a compound of general formula (I) in which $R_1$ represents:
  either an optionally substituted phenylmethyl group, by deprotecting the nitrogen of the piperidine ring, for example with an oxidizing agent or with a Lewis acid such as boron tribromide, or by hydrogenolysis,
  or an alkenyl group, preferably an allyl group, by deprotecting the nitrogen of the piperidine ring, for example with a $Pd^0$ complex, to obtain a compound of general formula (I) in which $R_1$ represents a hydrogen atom.

The piperidinone of general formula (XV) is commercially available.

Moreover, the chiral compounds of general formula (I) may be obtained by separation of the racemic compounds via high-performance liquid chromatography (HPLC) on a chiral column, or by resolution of the racemic amine of general formula (II) by using a chiral acid, such as tartaric acid, camphorsulfonic acid, dibenzoyltartaric acid or N-acetylleucine, via fractional and preferential recrystallization of a diastereoisomeric salt in a solvent of alcohol type.

The piperidines of general formula (IV) are prepared by protection, for example with a Boc group, of the nitrogen of the corresponding piperidines, which are commercially available or described in the literature, according to methods known to those skilled in the art. The method for forming the lithiopiperidine from the piperidine of general formula (IV) and its reaction with the benzaldehyde of general formula (VI) is similar to that described in J.O.C., 55, (1990), 2578-2580. The phenyllithium compound of general formula (VII) in which X represents a hydrogen atom is commercially available. Its substituted derivatives may be prepared according to a method similar to that described in Tetrahedron Lett., 57, 33, (1996), 5905-5908. The aldehydes of general formula (V) in which $R_2$ represents a methyl group in positions 2, 4, 5 and 6 are described in J.O.C., 58, (1993), 1109-117 and J. Chem. Soc., Perkin Trans. 1, (2002), 1438-1443. The halo derivatives of formula $R_1Z$ are commercially available. Certain acids and acid chlorides of general formula (III) are commercially available or, when they are novel, may be obtained according to methods similar to those described in patents EP-0 556 672 and U.S. Pat. No. 3,801,636 and in J. Chem.

Soc., (1927), 25, Chem. Pharm. Bull., (1992), 1789-1792, Aust. J. Chem., (1984), 1938-1950 and J.O.C., (1980), 527.

The examples that follow illustrate the preparation of a number of compounds of the invention. The elemental microanalyses, the IR and NMR spectra and the HPLC on a chiral column confirm the structures and the enantiomeric purities of the compounds obtained.

The numbers given in parentheses in the example titles correspond to those in the first column of the table given later.

In the compound names, the hyphen "–" forms part of the word, and the underscore mark "_" serves merely to indicate a line break; it should be deleted if a line break does not occur at that point, and should not be replaced either with a normal hyphen or with a space.

EXAMPLE 1

Compound 1

Cis-threo-2-chloro-N-[(1,6-dimethyl-2-piperidyl) (phenyl)methyl]-3-(trifluoromethyl)benzamide hydrochloride 1:1

1.1. 1,1-Dimethylethyl cis-[2-hydroxy(phenyl)me-thyl-6-methyl]piperidine-1-carboxylate 1 g (4.4 mmol) of 1,1-dimethylethyl cis-2-formyl-6-methylpiperidine-1-carboxylate is introduced into 15 ml of anhydrous tetrahydrofuran in a 50 ml round-bottomed flask, under a nitrogen atmosphere, the medium is cooled to −78° C., 4.4 ml (4.4 mmol) of a 1M solution of phenylmagnesium bromide in tetrahydrofuran are added dropwise and the mixture is allowed to warm to −50° C. with stirring for 2 hours.

After hydrolysis with saturated aqueous ammonium chloride solution, the aqueous phase is separated out and extracted with ethyl acetate. The combined organic phases are dried over sodium sulfate, filtered and concentrated under reduced pressure, and the residue is purified by column chromatography on silica gel, eluting with a mixture of ethyl acetate and cyclohexane. 1.15 g of alcohol are obtained in the form of a threo/erythro diastereoisomer mixture.

1.2. 1,1-Dimethylethyl cis-2-methyl-6-(phenylcarbonyl)piperidine-1-carboxylate 0.12 g (1.5 mmol) of sodium acetate suspended in 20 ml of dichloromethane, and 1.2 g (5.5 mmol) of pyridinium chlorochromate are successively introduced into a 100 ml round-bottomed flask, followed by addition of a solution of 1.15 g (3.76 mmol) of 1,1-dimethylethyl cis-[2-hydroxy(phenyl) methyl-6-methyl]piperidine-1-carboxylate in 20 ml of dichloromethane. The mixture rapidly turns black, and is left stirring for 4 hours at room temperature.

30 ml of ethyl ether are added, the mixture is filtered, rinsed and concentrated under reduced pressure, and the residue is purified by column chromatography on silica gel, eluting with a mixture of ethyl acetate and cyclohexane.

0.46 g of ketone is obtained in the form of a white solid.

Melting point: 92-93° C.

1.3. 1,1-Dimethylethyl cis-threo-[2-hydroxy(phenyl) methyl-6-methyl]piperidine-1-carboxylate 0.46 g (1.5 mmol) of 1,1-dimethylethyl cis-2-methyl-6-(phenylcarbonyl)-piperidine-1-carboxylate is introduced into 40 ml of anhydrous tetrahydrofuran in a 100 ml round-bottomed flask, the solution is cooled to −78° C., and 4.6 ml (4.6 mmol) of a 1M solution of L-Selectride® (lithium tri-sec-butylborohydride) in tetrahydrofuran are added dropwise, and the mixture is stirred at −78° C. for 5 hours.

The resulting mixture is hydrolyzed slowly under cold conditions with 3.2 ml of water and 3.2 ml of aqueous 35% hydrogen peroxide solution, and the mixture is allowed to return to room temperature with stirring for 2 hours.

The resulting mixture is diluted with water and ethyl acetate, the phases are separated and the aqueous phase is extracted with ethyl acetate. After washing the combined organic phases, drying over sodium sulfate, filtering and evaporating, the residue is purified by column chromatography on silica gel, eluting with a mixture of ethyl acetate and cyclohexane.

0.38 g of threo-cis isomer is obtained in the form of a colorless oil.

1.4. Cis-threo-(1,6-dimethyl-2-piperidyl)phenylmethanol 0.24 g (6.3 mmol) of lithium aluminum hydride is introduced into 7 ml of anhydrous tetrahydrofuran in a 25 ml two-necked flask, under a nitrogen atmosphere, the mixture is heated to reflux, 0.38 g (1.2 mmol) of a solution of 1,1-dimethylethyl cis-threo-[2-hydroxy(phenyl)methyl-6-methyl]piperidine-1-carboxylate in 3 ml of tetrahydrofuran is added and the mixture is maintained at reflux for 3.5 hours.

The resulting mixture is cooled and hydrolyzed slowly with 0.1M potassium sodium tartrate solution, and the mixture is stirred overnight. The resulting mixture is filtered, the precipitate is rinsed with tetrahydrofuran, the filtrate is concentrated under reduced pressure and the residue is purified by column chromatography on silica gel, eluting with a mixture of dichloromethane and methanol.

0.11 g of a colorless oily product is obtained.

1.5 Cis-threo-(1,6-dimethyl-2-piperidyl)phenylmethanamine 0.11 g (0.52 mmol) of cis-threo-(1,6-dimethyl-2-piperidyl) phenylmethanol and 0.11 ml (0.78 mmol) of triethylamine are introduced into 7 ml of anhydrous dichloromethane in a 25 ml round-bottomed flask under a nitrogen atmosphere, the medium is cooled to 0° C., 0.06 ml (0.78 mmol) of methanesulfonyl chloride is added and the mixture is allowed to return slowly to room temperature over 2 hours and concentrated under reduced pressure.

Liquefied ammonia is introduced into an autoclave equipped with a magnetic stirrer and cooled to −50° C., a solution of the crude methanesulfonate prepared above dissolved in 30 ml of absolute ethanol is added, the autoclave is closed and the mixture is stirred for 48 hours. The mixture is transferred into a round-bottomed flask and concentrated to dryness, the residue is diluted with water and dichloromethane, the phases are separated and the aqueous phase is extracted with dichloromethane. After washing the combined organic phases, drying over sodium sulfate, filtering and evaporating, 0.1 g of amine is isolated in the form of an oily compound, which is used without further purification in the following step.

1.6. Cis-threo-2-chloro-N-[(1,6-dimethyl-2-piperidyl)(phenyl)methyl]-3-(trifluoromethyl)benzamide hydrochloride 1:1

0.13 g (0.58 mmol) of 2-chloro-3-trifluoromethanebenzoic acid, 0.11 g (0.59 mmol) of 1-[3-(dimethylamine)propyl]-3-ethylcarbodiimide hydrochloride and 0.03 g (0.24 mmol) of dimethylaminopyridine dissolved in 4 ml of dichloromethane are successively introduced into a 25 ml round-bottomed flask, 0.10 g (0.48 mmol) of cis-threo-(1,6-dimethyl-2-piperidyl)phenylmethanamine dissolved in 1 ml of dichloromethane is added and the mixture is left stirring for 5 hours.

The resulting mixture is treated with water and extracted several times with dichloromethane. After washing the organic phases with water and then with aqueous 1N sodium hydroxide solution, drying over magnesium sulfate, filtering evaporating off the solvent under reduced pressure, the residue is purified by column chromatography on silica gel, eluting with a mixture of dichloromethane and methanol.

0.18 g of oily product is obtained, which is isolated in hydrochloride form from a 0.1N solution of hydrogen chloride in 2-propanol.

0.12 g of hydrochloride is finally isolated in the form of white solid.

Melting point: 208-209° C.

EXAMPLE 2

Compound 9

Cis-threo-2-chloro-N-[(1,4-dimethyl-2-piperidyl)(phenyl)methyl]-3-(trifluoromethyl)benzamide hydrochloride 1:1

2.1. Cis-7-methyl-1-phenylhexahydro[1,3]oxazolo[3,4-a]pyridin-3-one 14.2 g (71.2 mmol) of 1,1-dimethylethyl 4-methylpiperidine-1-carboxylate dissolved in 130 ml of anhydrous diethyl ether are introduced into a 1 l round-bottomed flask, under an argon atmosphere, and the medium is cooled to −70° C. 14 ml (92.5 mmol) of TMEDA (N,N,N',N'-tetramethylethylenediamine) are added, followed by addition of 70 ml (92.5 mmol) of a 1.3M solution of sec-butyllithium in cyclohexane, and the mixture is allowed to return to −30° C. with stirring over 0.5 hour.

A solution of 11.33 ml (106.8 mmol) of benzaldehyde (distilled beforehand) in 40 ml of anhydrous diethyl ether is then added and the mixture is allowed to return to room temperature with stirring over 12 hours.

After hydrolysis with water, the aqueous phase is separated out and extracted with ethyl acetate. The combined organic phases are dried over sodium sulfate, filtered and concentrated under reduced pressure, and the residue is purified by column chromatography on silica gel, eluting with a mixture of dichloromethane and methanol.

3.3 g of a colorless oil of a mixture of cis threo/erythro isomers are obtained.

2.2 Cis-threo-(1,4-dimethyl-2-piperidyl)phenylmethanol 2.71 g (71.5 mmol) of lithium aluminum hydride are introduced into 120 ml of anhydrous tetrahydrofuran in a 500 ml two-necked flask, under a nitrogen atmosphere, the mixture is heated to reflux, 3.33 g (14.3 mmol) of a solution of cis-7-methyl-1-phenylhexahydro[1,3]oxazolo[3,4-a]pyridin-3-one in 40 ml of tetrahydrofuran are added and refluxing is continued for 5.5 hours.

The mixture is cooled, hydrolyzed slowly with 0.1M potassium sodium tartrate solution and stirred overnight.

The resulting mixture is filtered, the precipitate is rinsed with tetrahydrofuran, the filtrate is concentrated under reduced pressure and the residue is purified by column chromatography on silica gel, eluting with a mixture of dichloromethane and methanol.

0.95 g of a product is obtained in the form of a colorless oil.

2.3. Cis-threo-(1,4-dimethyl-2-piperidyl)phenylmethanamine 0.95 g (4.3 mmol) of cis-threo-(1,4-dimethyl-2-piperidyl)phenylmethanol and 0.9 ml (6.5 mmol) of triethylamine are introduced into 40 ml of anhydrous dichloromethane in a 10 ml round-bottomed flask, under a nitrogen atmosphere, the medium is cooled to 0° C., 0.5 ml (6.5 mmol) of methanesulfonyl chloride is added and the mixture is allowed to return slowly to room temperature over 2 hours and is concentrated under reduced pressure.

Liquefied ammonia is introduced into an autoclave equipped with a magnetic stirrer and cooled to −50° C., a solution of the crude methanesulfonate prepared above dissolved in 30 ml of absolute ethanol is added, and the autoclave is closed and stirred for 48 hours. The mixture is transferred into a round-bottomed flask and concentrated to dryness, the residue is diluted with water and dichloromethane, the phases are separated and the aqueous phase is extracted with dichloromethane.

After washing the combined organic phases, drying over sodium sulfate, filtering and evaporating, 0.8 g of amine is isolated in the form of an oily compound, which is used without further purification in the following step.

2.4. Cis-threo-2-chloro-N-[(1,4-dimethyl-2-piperidyl)(phenyl)methyl]-3-(trifluoromethyl)benzamide hydrochloride 1:1

0.98 g (4.38 mmol) of 2-chloro-3-trifluoromethanebenzoic acid, 0.85 g (4.46 mmol) of 1-[3-(dimethylamine)propyl]-3-ethylcarbodiimide hydrochloride and 0.22 g (1.83 mmol) of dimethylaminopyridine dissolved in 20 ml of dichloromethane are successively introduced into a 50 ml round-bottomed flask, 0.8 g (3.66 mmol) of cis-threo-(1,4-dimethyl-2-piperidyl)phenylmethanamine dissolved in 4 ml of dichloromethane is added and the mixture is stirred for 12 hours.

The resulting mixture is treated with water and extracted several times with dichloromethane. After washing the organic phases with water and then with aqueous 1N sodium hydroxide solution, drying over magnesium sulfate, filtering and evaporating off the solvent under reduced pressure, the residue is purified by column chromatography on silica gel, eluting with a mixture of dichloromethane and methanol.

0.32 g of oily product is obtained, which is isolated in hydrochloride form from a 0.1N solution of hydrogen chloride in 2-propanol. 0.28 g of hydrochloride is finally isolated in the form of a white solid.

Melting point: 209-211° C.

EXAMPLE 3

Compound 5

Trans-threo-2-chloro-N-[(1,5-dimethyl-2-piperidyl)(4-fluorophenyl)methyl]-3-(trifluoromethyl)benzamide hydrochloride 1:1

By working in the same manner as in Example 2 and replacing the 1,1-dimethylethyl 4-methylpiperidine-1-carboxylate with 1,1-dimethylethyl 5-methylpiperidine-1-carboxylate and the benzaldehyde with 4-fluorobenzaldehyde, a mixture of corresponding alcohol and isoxazolidone is obtained. Reduction of the isoxazolidone obtained with lithium aluminum hydride gives the trans-threo amino alcohol compound, which is used according to the methods described in steps 2.3 and 2.4 of Example 2 using 2-chloro-3-trifluoromethanebenzoic acid.

Melting point: 220-222° C.

EXAMPLE 4

Compound 10

Threo-2-chloro-N-[(1,2-dimethyl-2-piperidyl)(phenyl)methyl]-3-(trifluoromethyl)benzamide hydrochloride 1:1

4.1. 1,2-Dimethylpiperidine-2-carbonitrile 22 ml (31 mmol) of a 1.4M solution of methylmagnesium bromide in tetrahydrofuran are introduced into a 500 ml three-necked flask equipped with a condenser and a magnetic stirrer, under a nitrogen atmosphere, followed by addition of a solution of 5 g (44.2 mmol) of 1-methylpiperidin-2-one in 20 ml of tetrahydrofuran, and the mixture is refluxed with stirring for 2 hours.

The mixture is allowed to cool, 50 ml of 2N hydrochloric acid solution are added and the resulting mixture is extracted with ethyl acetate. The aqueous phase is then adjusted to pH 6 with sodium bicarbonate and 2.9 g (2.8 mmol) of potassium cyanide are added. The mixture is then stirred at 25° C. for 12 hours.

10% sodium bicarbonate solution is added and the mixture is extracted with ethyl acetate. After washing the combined organic phases, drying over sodium sulfate, filtering and evaporating, 3 g of product are obtained in the form of an oily compound, which is used without further purification in the following step.

4.2. 1-(1,2-Dimethyl-2-piperidyl)-1-phenylmethanamine

A solution of phenyllithium is prepared at −78° C. starting with 6.8 g (43.4 mmol) of bromobenzene in 50 ml of tetrahydrofuran and 17.4 ml of butyllithium (2.5M in hexane), in a 250 ml round-bottomed flask equipped with a magnetic stirrer and under an argon atmosphere. A solution of 3 g (21.71 mmol) of 1,2-dimethylpiperidine-2-carbonitrile in 50 ml of tetrahydrofuran is introduced at 78° C. and the mixture (yellow solution) is stirred and allowed to return to room temperature over 1 hour. Water is added and the resulting mixture is extracted with ethyl acetate. The combined organic phases are dried over sodium sulfate and filtered, and the imine is concentrated under reduced pressure. The residue is taken up in a 250 ml round-bottomed flask with 50 ml of methanol. The mixture is cooled to 0° C. and 4 g (108 mmol) of sodium borohydride are added slowly. Stirring is continued while allowing the temperature of the mixture to return to room temperature over 1 hour. The mixture is concentrated under reduced pressure and the residue is taken up in water and ethyl acetate. The phases are separated and the aqueous phase is extracted with ethyl acetate. After washing the combined organic phases, drying over sodium sulfate, filtering and evaporating, 3.2 g of product are obtained in the form of an oily compound, which is used without further purification in the following step.

4.3. Threo-2-chloro-N-[(1,2-dimethyl-2-piperidyl)(phenyl)methyl]-3-(trifluoromethyl)benzamide hydrochloride 1:1

0.41 g (1.8 mmol) of 1-(1,2-dimethyl-2-piperidyl)-1-phenylmethanamine, 0.3 ml (2.25 mmol) of triethylamine and 0.54 g (2.25 mmol) of 2-chloro-3-(trifluoromethyl)benzoyl chloride are successively introduced into 20 ml of dichloromethane in a 100 ml round-bottomed flask, and the mixture is stirred at room temperature for 1 hour.

The resulting mixture is treated with water and extracted several times with dichloromethane. After washing the organic phases with water and then with aqueous 1N sodium hydroxide solution, drying over magnesium sulfate, filtering and evaporating off the solvent under reduced pressure, the residue is purified by column chromatography on silica gel, eluting with a mixture of dichloromethane and methanol.

0.36 g of oily product is obtained.

This product is converted into the hydrochloride using a 0.1N solution of hydrogen chloride in 2-propanol.

0.14 g of hydrochloride is finally isolated in the form of a white solid.

Melting point: 239-241° C.

The table that follows illustrates the chemical structures and the physical properties of a number of compounds of the invention.

In the "salt" column, "HCl" denotes a hydrochloride.

TABLE

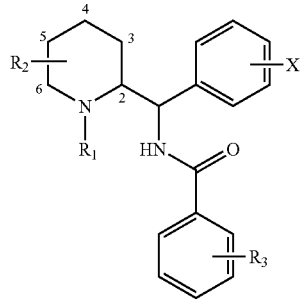

(I)

| No. | $R_1$ | X | $R_2$ | $R_3$ | Salt | M.p. (° C.) | Stereochemistry |
|---|---|---|---|---|---|---|---|
| 1 | $CH_3$ | H | Cis 6-$CH_3$ | 2-Cl, 3-$CF_3$ | HCl | 208-209 | Threo |
| 2 | $CH_3$ | H | Trans 6-$CH_3$ | 2-Cl, 3-$CF_3$ | HCl | 128-129 | Threo |
| 3 | $CH_3$ | H | Trans 6-$CH_2$—C6H11 | 2-Cl, 3-$CF_3$ | HCl | 127-129 | Threo |
| 4 | $CH_3$ | H | Trans 6-$CH_3$ | 3,5-Cl, 4-$NH_2$ | HCl | 270-271 | Threo |
| 5 | $CH_3$ | 4-F | Trans 5-$CH_3$ | 2-Cl, 3-$CF_3$ | HCl | 220-222 | Threo |
| 6 | $CH_3$ | 4-F | Trans 5-$CH_3$ | 3-Cl, 4-$NH_2$ | HCl | 169-171 | Threo |
| 7 | $CH_3$ | H | Cis 5-$CH_3$ | 2-$CH_3$, 3-$CF_3$ | HCl | 131-133 | Threo |
| 8 | $CH_3$ | 4-F | Cis 6-$CH_3$ | 3,5-Cl, 4-$NH_2$ | HCl | 254-256 | Threo |
| 9 | $CH_3$ | H | Cis 4-$CH_3$ | 2-Cl, 3-$CF_3$ | HCl | 209-211 | Threo |
| 10 | $CH_3$ | H | 2-$CH_3$ | 2-Cl, 3-$CF_3$ | HCl | 239-241 | Threo |
| 11 | $CH_3$ | H | 2-$CH_3$ | 2-Cl, 3-$CH_3$, 6-F | HCl | 227-229 | Threo |
| 12 | $CH_3$ | H | 2-$CH_3$ | 2-$CH_3$, 3-$CF_3$ | HCl | 149-151 | Threo |
| 13 | $CH_3$ | H | 2-$CH_3$ | 2-$CH_3$, 3-$OCH_3$ | HCl | 170-172 | Threo |
| 14 | $CH_3$ | H | 2-$CH_3$ | 2-$CH_3$, 3-Cl | HCl | 177-179 | Threo |
| 15 | $CH_3$ | H | 2-$CH_3$ | 2-Cl, 5-$CF_3$ | HCl | 213-215 | Threo |
| 16 | $CH_3$ | H | 2-$CH_3$ | 2,6-Cl, 3-$CF_3$ | HCl | 253-255 | Threo |
| 17 | $CH_2CH:CH_2$ | H | 2-$CH_3$ | 2-Cl, 3-$CF_3$ | HCl | 244-246 | Threo |
| 18 | H | H | 2-$CH_3$ | 2-Cl, 3-$CF_3$ | HCl | 278-280 | Threo |

The compounds of the invention were subjected to a series of pharmacological tests that demonstrated their value as therapeutically active substances.

Study of Glycine Transportation in SK-N-MC Cells Expressing the Native Human Transporter glyt1

The uptake of [$^{14}$C]glycine is studied in SK-N-MC cells (human neuroepithelial cells) expressing the native human transporter glyt1 by measuring the radioactivity incorporated in the presence or absence of the test compound. The cells are cultured as a monolayer for 48 hours in plates pretreated with 0.02% fibronectin. On the day of the experiment, the culture medium is removed and the cells are washed with Krebs-HEPES buffer ([4-(2-hydroxyethyl)-1-piperazineethanesulfonic acid) at pH 7.4. After preincubation for 10 minutes at 37° C. in the presence either of buffer (control batch) or of test compound at various concentrations or of 10 mM glycine (determination of the nonspecific uptake), 10 µM of [$^{14}$C] glycine (specific activity 112 mCi/mmol) are then added.

Incubation is continued for 10 minutes at 37° C., and the reaction is quenched by washing twice with pH 7.4 Krebs-HEPES buffer. The radioactivity incorporated by the cells is then estimated after adding 100 µl of liquid scintillant and stirring for 1 hour. Counting is performed on a Microbeta Tri-Lux™ counter. The efficacy of the compound is determined by means of the $IC_{50}$, which is the concentration of compound that reduces by 50% the specific uptake of glycine, defined by the difference in radioactivity incorporated by the control batch and the batch that received 10 mM of glycine.

The compounds of the invention that are the most active, in this test, have an $IC_{50}$ of about from 0.001 to 10 µM.

The individual results of a few compounds are as follows ($IC_{50}$ in µM):

| Compound 1 | 0.51 |
| Compound 5 | 0.1 |
| Compound 9 | 0.09 |
| Compound 10 | 0.008 |

Ex-Vivo Study of the Inhibitory Activity of a Compound on the Uptake of [$^{14}$C]Glycine in Mouse Cortex Homogenate Increasing doses of the compound to be studied are administered orally (preparation by trituration of the test molecule in a mortar in a 0.5% solution of Tween/Methocel™ in distilled water) or intraperitoneally (dissolution of the test molecule in physiological saline or preparation by trituration in a mortar in a 0.5% solution of Tween/Methocel in water, according to the solubility of the molecule) on male OF1 Iffa Credo mice weighing 20 to 25 g on the day of the experiment. The control group is treated with the vehicle. The doses in mg/kg, the route of administration and the treatment time are determined as a function of the molecule to be studied. After euthanasia by decapitation of the animals at a given time after the administration, the cortex of each animal is rapidly removed onto ice, weighed and stored at 4° C. or frozen at −80° C. (in both cases the samples are stored for a maximum of 1 day). Each sample is homogenized in pH 7.4 Krebs-HEPES buffer in a proportion of 10 ml/g of tissue. 20 µl of each homogenate are incubated for 10 minutes at room temperature in the presence of 10 mM of L-alanine and of buffer. The nonspecific uptake is determined by addition of 10 mM of glycine to the control group. The reaction is quenched by vacuum filtration and the radioactivity retained is estimated by solid scintillation by counting using a Microbeta Tri-lux™ counter. An inhibitor of the uptake of [$^{14}$C]glycine will reduce the amount of radioligand incorporated into each homogenate. The activity of the compound is evaluated by means of its $ED_{50}$, the dose that inhibits 50% of the uptake of [$^{14}$C] glycine relative to the control group.

The compounds of the invention that are the most powerful in this test have an $ED_{50}$ of from 0.1 to 5 mg/kg intraperitoneally or orally.

Study of the Glycine Transportation in Mouse Spinal Cord Homogenate

The uptake of [$^{14}$C]glycine by the transporter glyt2 is studied in mouse spinal cord homogenate by measuring the radioactivity incorporated in the presence or absence of test compound.

After euthanizing the animals (male OF1 Iffa Credo mice weighing 20 to 25 g on the day of the experiment), the spinal cord of each animal is rapidly removed, weighed and stored on ice. The samples are homogenized in pH 7.4 Krebs-HEPES buffer ([4-(2-hydroxyethyl)-1-piperazineethanesulfonic acid), in a proportion of 25 ml/g of tissue.

50 µl of homogenate are preincubated for 10 minutes at 25° C. in the presence of pH 7.4 Krebs-HEPES buffer and of test compound at various concentrations, or of 10 mM of glycine to determine the nonspecific uptake. [$^{14}$C]glycine (specific activity=112 mCi/mmol) is then added over 10 minutes at 25° C. to a final concentration of 10 µM. The reaction is quenched by vacuum filtration and the radioactivity is estimated by solid scintillation by counting on a Microbeta Tri-Lux™ counter. The efficacy of the compound is determined by means of the $IC_{50}$, the concentration capable of reducing by 50% the specific uptake of glycine, defined by the difference in radioactivity incorporated by the control batch and the batch that received 10 mM of glycine.

The compounds of the invention that are the most active in this test have an $IC_{50}$ of about from 0.001 to 10 µM.

The individual results of a few compounds are as follows ($IC_{50}$ in µM):

| | |
|---|---|
| Compound 1 | 0.12 |
| Compound 9 | 0.07 |

Ex-Vivo Study of the Inhibitory Activity of a Compound on the Uptake of [$^{14}$C]Glycine in Mouse Spinal Homogenate Increasing doses of the compound to be studied are administered orally (preparation by triturating the test compound in a mortar, in a 0.5% solution of Tween/Methocel™ in distilled water) or intraperitoneally (test compound dissolved in physiological saline, or triturated in a mortar, in a 0.5% solution of Tween/Methocel™ in distilled water) to male OF1 Iffa Credo mice weighing 20 to 25 g on the day of the experiment. The control group is treated with the vehicle. The doses in mg/kg, the route of administration, the treatment time and the euthanasia time are determined as a function of the compound to be studied.

After euthanasia by decapitation of the animals at a given time after the administration, the spinal cords are rapidly removed, weighed and introduced into glass scintillation flasks, stored in crushed ice or frozen at −80° C. (in both cases the samples are stored for a maximum of 1 day). Each sample is homogenized in pH 7.4 Krebs-HEPES buffer, in a proportion of 25 ml/g of tissue. 50 µl of each homogenate are incubated for 10 minutes at room temperature in the presence of buffer.

The nonspecific uptake is determined by adding 10 mM of glycine to the control group.

The reaction is quenched by vacuum filtration and the radioactivity is estimated by solid scintillation by counting on a Microbeta Tri-lux™ counter.

An inhibitor of the uptake of [$^{14}$C]glycine will reduce the amount of radioligand incorporated into each homogenate. The activity of the compound is evaluated by means of its $ED_{50}$, the effective dose that inhibits 50% of the uptake of [$^{14}$C]glycine relative to the control group.

The compounds of the invention that are the most active in this test have an $ED_{50}$ of from 1 to 20 mg/kg intraperitoneally or orally.

The results of the tests performed on the compounds of the invention show that they are inhibitors of the glycine transporters glyt1 present in the brain and glyt2 present in the brain or the spinal cord.

The compounds according to the invention may thus be used for the preparation of medicaments, in particular of medicaments that inhibit the glycine transporters glyt1 and/or glyt2.

Thus, according to another of its aspects, a subject of the invention is medicaments comprising a compound of formula (I), or an addition salt thereof with a pharmaceutically acceptable acid, or alternatively a hydrate or a solvate of the compound of formula (I).

The compounds of the invention may be used especially for behavioral disorders associated with dementia, psychoses, in particular schizophrenia (deficient form and productive form) and acute or chronic extrapyramidal symptoms induced by neuroleptics, for the treatment of various forms of anxiety, panic attacks, phobia, obsessive compulsive disorders, for treating various forms of depression, including psychotic depression, for treating disorders caused by alcohol abuse or weaning from alcohol, sexual behavior disorders, eating disorders and for treating migraine.

Moreover, the compounds of the invention may be used for treating painful muscle contracture in rheumatology and in acute spinal pathology, for treating spastic contractures of medullary or cerebral origin, for the symptomatic treatment of acute and subacute pain of light to moderate intensity, for treating intense and/or chronic pain, neurogenic pain and intractable pain, for treating Parkinson's disease and Parkinson-like symptoms of neurodegenerative origin or induced by neuroleptics, for treating partial primary and secondary generalized epilepsy of simple or complex symptomatology, mixed forms and other epileptic syndromes in addition to another antiepileptic treatment, or in monotherapy, for the treatment of sleep apnea, and for neuroprotection.

A subject of the present invention is also pharmaceutical compositions containing an effective dose of at least one compound according to the invention, in the form of base or of pharmaceutically acceptable salt or solvate, and as a mixture, where appropriate, with suitable excipients. Said excipients are chosen according to the pharmaceutical form and the desired mode of administration.

The pharmaceutical compositions according to the invention may thus be intended for oral, sublingual, subcutaneous, intramuscular, intravenous, topical, intra-tracheal, intranasal, transdermal, rectal or intraocular administration.

The unit administration forms may be, for example, tablets, gel capsules, granules, powders, oral or injectable solutions or suspensions, transdermal patches or suppositories. Pomades, lotions and eyedrops may be envisioned for topical administration.

By way of example, a unit form of administration of a compound according to the invention in the form of a tablet may comprise the following components:

| | |
|---|---|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

Said unit forms are dosed to allow a daily administration of from 0.01 to 20 mg of active principle per kg of body weight, according to the galenical form.

There may be special cases in which higher or lower doses are appropriate; such doses do not depart from the context of the invention. According to the usual practice, the dosage that is appropriate to each patient is determined by the medical practitioner according to the mode of administration, the weight and the response of said patient.

According to another of its aspects, the present invention also relates to a method for treating the pathologies indicated above, which comprises the administration, to a patient, of an effective dose of a compound according to the invention, or of a pharmaceutically acceptable salt or hydrates or solvates thereof.

The invention claimed is:

1. A compound of formula (I)

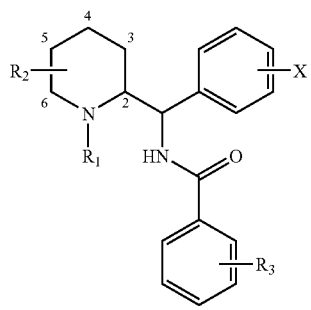

(I)

in which $R_1$ represents either a hydrogen atom, or a linear or branched $(C_1-C_7)$alkyl group optionally substituted with one or more fluorine atoms, or a $(C_3-C_7)$cycloalkyl group, or a $(C_3-C_7)$cycloalkyl$(C_1-C_3)$alkyl group, or a phenyl$(C_1-C_3)$alkyl group optionally substituted with one or two methoxy groups, or a $(C_2-C_4)$alkenyl group, or a $(C_2-C_4)$alkynyl group;

$R_2$ represents either a linear or branched $(C_1-C_7)$alkyl or $(C_3-C_7)$cycloalkyl group, or a $(C_3-C_7)$cycloalkyl$(C_1-C_3)$alkyl group;

X represents either a hydrogen atom or one or more substituents chosen from halogen atoms and trifluoromethyl, linear or branched $(C_1-C_6)$alkyl and $(C_1-C_6)$alkoxy groups;

$R_3$ represents either a hydrogen atom or one or more substituents chosen from halogen atoms and trifluoromethyl, linear or branched $(C_1-C_6)$alkyl, $(C_3-C_7)$cycloalkyl, $(C_1-C_6)$alkoxy, phenyl, cyano, acetyl, benzoyl, $(C_1-C_6)$thioalkyl, $(C_1-C_6)$alkylsulfonyl, carboxyl and $(C_1-C_6)$alkoxycarbonyl groups, or a group of general formula $NR_4R_5$ or $SO_2NR_4R_5$ or $CONR_4R_5$ in which $R_4$ and $R_5$ each independently represent a hydrogen atom or a linear or branched $(C_1-C_6)$alkyl or $(C_3-C_7)$cycloalkyl group, or $R_4$ and $R_5$ form, with the nitrogen atom that bears them, a pyrrolidine, piperidine or morpholine ring; in the form of free base or acid-addition salt.

2. A compound as claimed in claim 1, which is in the threo configuration; in the form of free base or acid-addition salt.

3. A compound as claimed in claim 2, which is of (1S,2S) or (1R,2R) configuration; in the form of free base or acid-addition salt.

4. A compound as claimed in claim 1, which is of erythro configuration; in the form of free base or acid-addition salt.

5. A compound as claimed in claim 4, which is of (1S,2R) or (1R,2S) configuration; in the form of free base or acid-addition salt.

6. A compound selected from the group consisting of:
cis-threo-2-chloro-N-[(1,6-dimethyl-2-piperidyl)(phenyl)methyl]-3-(trifluoromethyl)benzamide;
cis-threo-2-chloro-N-[(1,4-dimethyl-2-piperidyl)(phenyl)methyl]-3-(trifluoromethyl)benzamide;
trans-threo-2-chloro-N-[(1,5-dimethyl-2-piperidyl)(4-fluorophenyl)methyl]-3-(trifluoromethyl)benzamide; and
threo-2-chloro-N-[(1,2-dimethyl-2-piperidyl)(phenyl)methyl]-3-(trifluoromethyl)benzamide;
wherein said compound is in the form of free base or acid-addition salt.

7. A pharmaceutical composition which comprises a compound as claimed in claim 1, or a pharmaceutically acceptable salt of said compound and at least one pharmaceutically acceptable excipient.

8. A method treating a behavioral disorder selected from psychoses, schizophrenia, various forms of anxiety, and various forms of depression, which comprises, administering to a patient with said disorder an effective amount of a compound as claimed in claim 1.

* * * * *